(12) United States Patent
Duda et al.

(10) Patent No.: US 6,714,821 B1
(45) Date of Patent: Mar. 30, 2004

(54) HEATING PAD ASSEMBLY

(76) Inventors: Karl A. Duda, 74 Carlyle Ave., Coldwater, MI (US) 49036; Kami Duda, 74 Carlyle Ave., Coldwater, MI (US) 49036

( * ) Notice: Subject to any disclaimer, the term of this patent is extended or adjusted under 35 U.S.C. 154(b) by 27 days.

(21) Appl. No.: 10/158,952

(22) Filed: May 31, 2002

(51) Int. Cl.[7] ................................................. A61F 7/00
(52) U.S. Cl. ........................ 607/98; 607/108; 607/114
(58) Field of Search ........................... 607/98, 108, 99, 607/96, 114

(56) References Cited

U.S. PATENT DOCUMENTS

| | | | | |
|---|---|---|---|---|
| 2,869,551 | A | * | 1/1959 | Chandler ..................... 607/108 |
| 3,014,117 | A | * | 12/1961 | Madding ..................... 392/443 |
| 4,887,326 | A | | 12/1989 | O'Brien et al. |
| D324,734 | S | | 3/1992 | Burgess |
| 5,174,285 | A | | 12/1992 | Fontenot |
| 5,415,624 | A | * | 5/1995 | Williams ..................... 602/21 |
| 5,643,336 | A | | 7/1997 | Lopez-Claros |
| 5,755,275 | A | | 5/1998 | Rose et al. |
| 5,835,983 | A | * | 11/1998 | McMahen et al. ............ 607/98 |
| 5,840,080 | A | | 11/1998 | Der Ovanesian |
| 5,928,275 | A | * | 7/1999 | Yates et al. .................. 607/112 |
| 6,235,049 | B1 | * | 5/2001 | Nazerian ..................... 607/108 |
| 6,409,748 | B1 | * | 6/2002 | DeCarlo et al. ............. 607/114 |
| 6,416,534 | B1 | * | 7/2002 | Montagnino et al. ....... 607/114 |

* cited by examiner

Primary Examiner—Beverly M. Flanagan

(57) ABSTRACT

A heating pad assembly includes a cover member designed for abutting the back of a user. The cover member defines an interior space. A heating assembly is positioned within the cover member. The heating assembly has a first portion and a second portion. The first portion is positioned on a first side of the interior space. The second portion is positioned on a second side of the interior space. The first and second portions are positioned such that a center column through the interior space does not have either the first or second portions of the heating assembly positioned therein. A cord assembly is operationally coupled to the heating assembly. The cord assembly is designed for coupling to a conventional household electrical outlet. The cord assembly facilitates flow of electrical current through the heating assembly.

7 Claims, 3 Drawing Sheets

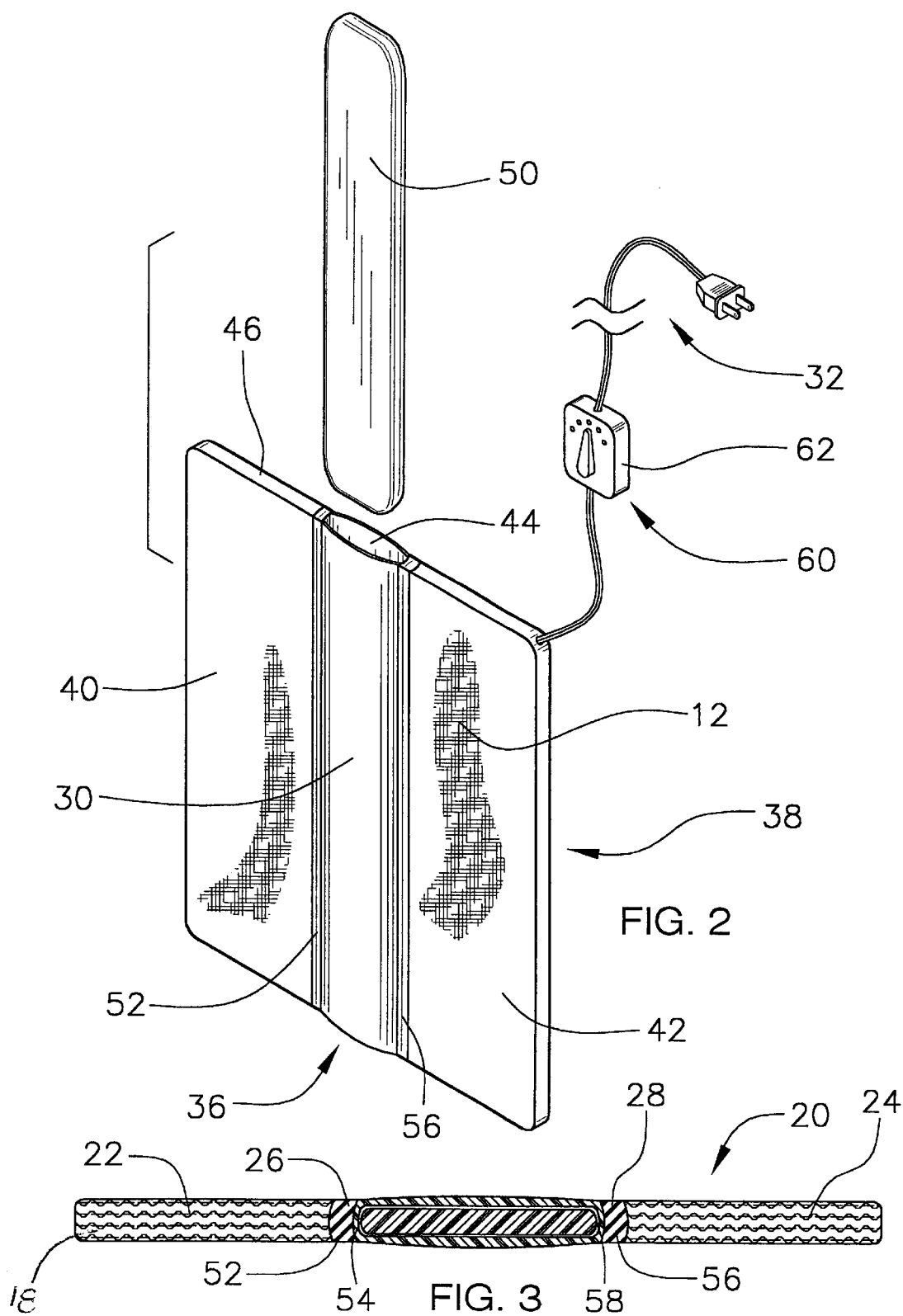

HEATING PAD ASSEMBLY

BACKGROUND OF THE INVENTION

1. Field of the Invention

The present invention relates to heating pads and more particularly pertains to a new heating pad assembly for providing a user with a therapeutic device designed to apply heat therapy to the body, primarily the back.

2. Description of the Prior Art

The use of heating pads is known in the prior art. U.S. Pat. No. 5,840,080 describes a hot or cold applicator with inner element for heating or cooling a surface such as the skin. Another type of heating pad is U.S. Pat. No. 5,755,275 describes tubed lamination heat transfer articles and method of manufacture that modulates the flow of heat to or from a human body. U.S. Pat. No. 4,887,326 describes a suboccipital pillow from applying hot and or cold treatments to the neck and suboccipatal areas. U.S. Pat. No. 5,174,285 describes a localized heat transfer device for tropically heating or cooling an animal or human body. U.S. Pat. No. 5,643,336 describes a heating and cooling pad for therapeutically treating regions about a patient's head. U.S. Pat. No. Des. 324,734 describes an ornamental design for cervical heat collar.

SUMMARY OF THE INVENTION

The object of the present invention is to provide a new heating pad assembly that would surround the painful area, providing heat more consistently and without the need for constant adjustments.

Another object of the present invention is to provide a new heating pad assembly that would feature a center column that would prevent heat from being applied to spinal nerves, providing more beneficial, therapeutic treatment.

To this end, the present invention generally comprises a cover member designed for abutting the back of a user. The cover member defines an interior space. A heating assembly is positioned within the cover member. The heating assembly has a first portion and a second portion. The first portion is positioned on a first side of the interior space. The second portion is positioned on a second side of the interior space. The first and second portions are positioned such that a center column through the interior space does not have either the first or second portions of the heating assembly positioned therein. A cord assembly is operationally coupled to the heating assembly. The cord assembly is designed for coupling to a conventional household electrical outlet. The cord assembly facilitates flow of electrical current through the heating assembly.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a perspective view of the present invention.

FIG. 3 is a cross-sectional view of the present invention.

DESCRIPTION OF THE PREFERRED EMBODIMENT

Figure 1:
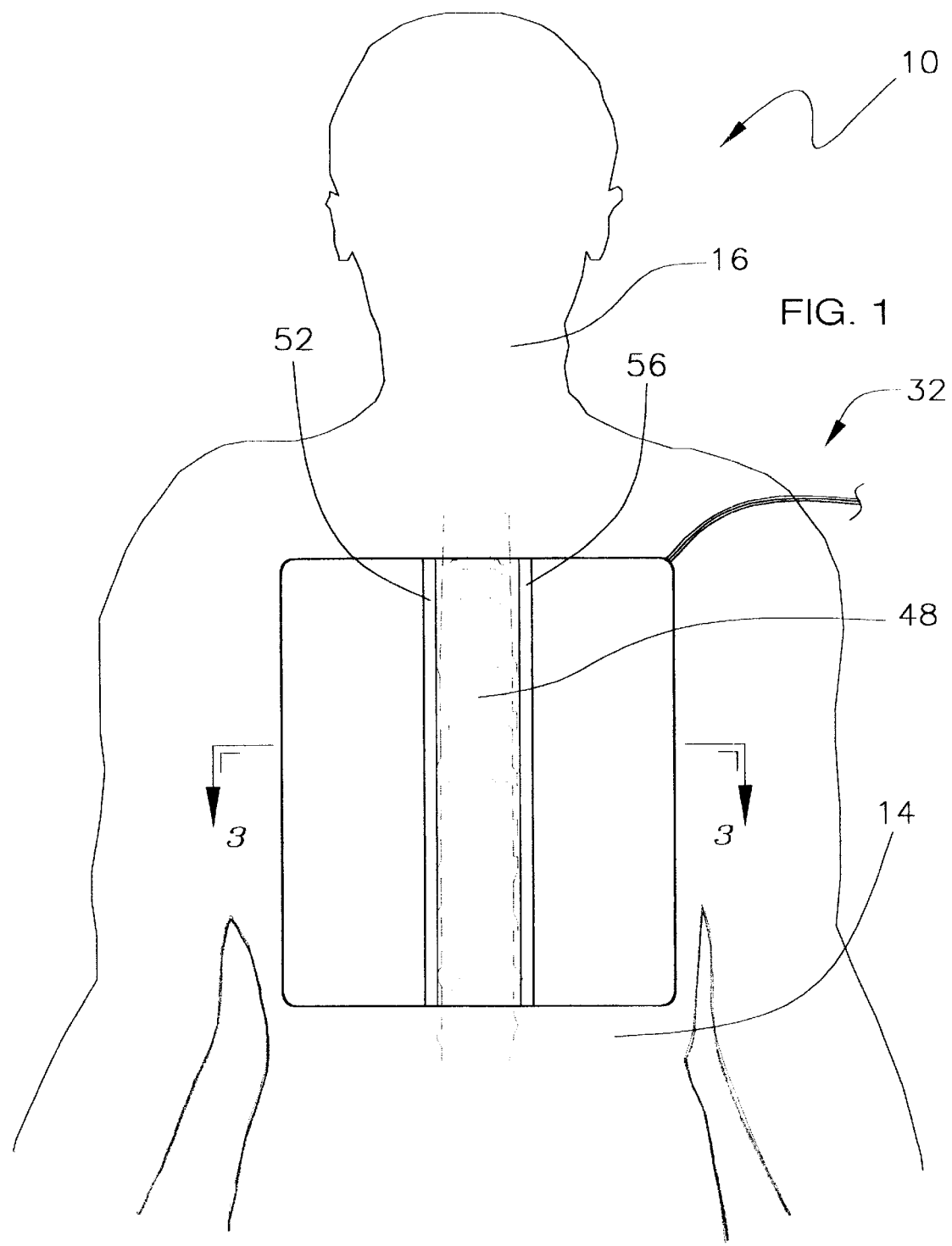
FIG. 1 is an in-use view of a new heating pad assembly according to the present invention.
Figure 4:
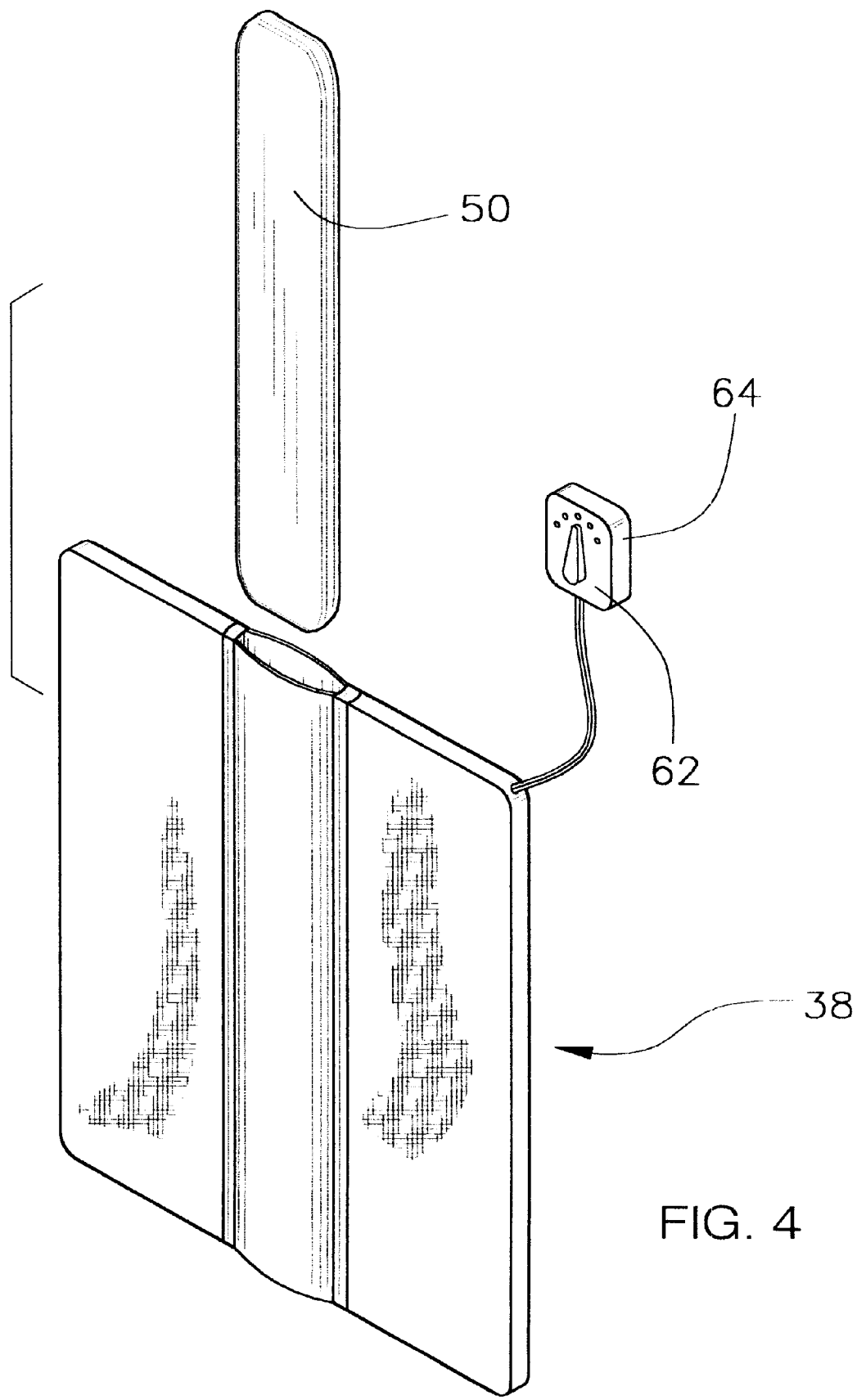
FIG. 4 is a perspective view of the present invention.

With reference now to the drawings, and in particular to FIGS. 1 through 4 thereof, a new heating pad assembly embodying the principles and concepts of the present invention and generally designated by the reference numeral 10 will be described.

As best illustrated in FIGS. 1 through 4, the heating pad assembly 10 generally comprises a cover member 12 designed for abutting the back 14 of a user 16. The cover member 12 defines an interior space 18. A heating assembly 20 is positioned within the cover member 12. The heating assembly 20 has a first portion 22 and a second portion 24. The first portion 22 is positioned on a first side 26 of the interior space 18. The second portion 24 is positioned on a second side 28 of the interior space 18. The first 22 and second 24 portions are positioned such that a center column 30 through the interior space 18 does not have either the first 22 or second 24 portions of the heating assembly 20 positioned therein. A cord assembly 32 is operationally coupled to the heating assembly 20. The cord assembly 32 is designed for coupling to a conventional household electrical outlet. The cord assembly 32 facilitates flow of electrical current through the heating assembly 20.

A pocket assembly 36 is coupled to the cover member 12. The pocket assembly 36 divides the cover assembly 38 into a first 40 and second 42 portion. The pocket assembly 36 is positioned in the center column 30. The pocket assembly 36 has an opening 44 adjacent to a top edge 46 of the cover member 12. The pocket assembly 36 is designed for abutting a spine 48 of the user 16.

A gel package 50 is positionable within the pocket assembly 36. The gel package 50 provides support for the spine 48 of the user 16 when the user 16 is in a reclined position abutting the assembly. The gel package 50 is removable from the pocket assembly 36. The gel package 50 is designed to be refrigerated such that the gel package 50 providing a cooling surface area when positioned in the pocket assembly 36.

A first insulator member 52 is positioned between a first edge 54 of the pocket assembly 36 and a first portion 40 of the cover member 12. The first insulator member 52 provides a thermal barrier between the heating assembly 20 and the gel package 50 such that heat generated by the heating assembly 20 is not conducted to the spine 48 of the user 16 when the gel package 50 abuts the spine 48.

A second insulator member 56 is positioned between a second edge 58 of the pocket assembly 36 and a second portion 42 of the cover member 12. The second insulator member 56 provides a thermal barrier between the heating assembly 20 and the gel package 50 such that heat generated by the heating assembly 20 is not conducted to the spine 48 of the user 16 when the gel package 50 abuts the spine 48.

A rheostat assembly 60 is operationally coupled to the heating assembly 20. The rheostat portion 62 is for adjusting a quantity of heat generated by the heating assembly 20 such that a temperature is adjustable by the user 16.

The cover member 12 has an overall height of approximately 20 inches. The cover member 12 has a length of approximately 14 inches, and an overall thickness of approximately ¾ inches.

A battery assembly 64 is operationally coupled to the heating assembly 20. The battery assembly 64 providing electrical current to the heating assembly 20.

In use, the present invention would be used similarly to a conventional heating pad.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A heating pad assembly for applying heat to a back of a user while isolating the user's spine comprising:
   a cover member adapted for abutting the back of a user, said cover member defining an interior space;
   a heating assembly positioned within said cover member, said heating assembly having a first portion and a second portion, said first portion being positioned on a first side of said interior space, said second portion being positioned on a second side of said interior space, said first and second portions being positioned such that a center column through said interior space does not have either said first or second portions of said heating assembly positioned therein;
   a cord assembly operationally coupled to said heating assembly, said cord assembly being adapted for coupling to a conventional household electrical outlet, said cord assembly facilitating flow of electrical current through said heating assembly;
   a pocket assembly coupled to said cover member, said pocket assembly dividing said cover assembly into a first and second portions, said pocket assembly being positioned in said center column, said pocket assembly having an opening adjacent to a top edge of said cover member, said pocket assembly being adapted for abutting a spine of the user; and
   a gel package positionable within said pocket assembly, said gel, said gel package providing support for the spine of the user when the user is in a reclined position abutting said assembly.

2. The assembly of claim 1, wherein said gel package being removable from said pocket assembly, said gel package being adapted for being refrigerated such that said gel package providing a cooling surface area when positioned in said pocket assembly.

3. The assembly of claim 1, further comprising:
   a first insulator member positioned between a first edge of said pocket assembly an a first portion of said cover member, said first insulator member providing a thermal barrier between said heating assembly and said gel package such that heat generated by said heating assembly is not conducted to the spine of the user when said gel package abuts the spine; and
   a second insulator member positioned between a second edge of said pocket assembly and a second portion of said cover member, said second insulator member providing a thermal barrier between said heating assembly and said gel package such that heat generated by said heating assembly is not conducted to the spine of the user when said gel package abuts the spine.

4. The assembly of claim 1, further comprising a rheostat assembly operationally coupled to said heating assembly, said rheostat portion being for adjusting a quantity of heat generated by said heating assembly such that a temperature is adjustable by the user.

5. A heating pad assembly for applying heat to a back of a user while isolating the user's spine comprising:
   a cover member adapted for abutting the back of a user, said cover member defining an interior space;
   a heating assembly positioned within said cover member, said heating assembly having a first portion and a second portion, said first portion being positioned on a first side of said interior space, said second portion being positioned on a second side of said interior space, said first and second portions being positioned such that a center column through said interior space does not have either said first or second portions of said heating assembly positioned therein; and
   a cord assembly operationally coupled to said heating assembly, said cord assembly being adapted for coupling to a conventional household electrical outlet, said cord assembly facilitating flow of electrical current through said heating assembly;
   wherein a pocket assembly coupled to said cover member, said pocket assembly dividing said cover assembly into a first and second portions, said pocket assembly being positioned in said center column, said pocket assembly having an opening adjacent to a top edge of said cover member, said pocket assembly being adapted for abutting a spine of the user; and
   a gel package positionable within said pocket assembly, said gel, said gel package providing support for the spine of the user when the user is in a reclined position abutting said assembly;
   wherein said gel package being removable from said pocket assembly, said gel package being adapted for being refrigerated such that said gel package providing a cooling surface area when positioned in said pocket assembly;
   wherein a first insulator member positioned between a first edge of said pocket assembly an a first portion of said cover member, said first insulator member providing a thermal barrier between said heating assembly and said gel package such that heat generated by said heating assembly is not conducted to the spine of the user when said gel package abuts the spine; and
   a second insulator member positioned between a second edge of said pocket assembly an a second portion of said cover member, said second insulator member providing a thermal barrier between said heating assembly and said gel package such that heat generated by said heating assembly is not conducted to the spine of the user when said gel package abuts the spine; and
   wherein a rheostat assembly operationally coupled to said heating assembly, said rheostat portion being for adjusting a quantity of heat generated by said heating assembly such that a temperature is adjustable by the user.

6. The assembly of claim 5, wherein said cover member having an overall height of approximately 20 inches, said cover member having a length of approximately 14 inches, and said cover member having an overall thickness of approximately ¾ inches.

7. A heating pad assembly for applying heat to a back of a user while isolating the user's spine comprising:

- a cover member adapted for abutting the back of a user, said cover member defining an interior space;
- a heating assembly positioned within said cover member, said heating assembly having a first portion and a second portion, said first portion being positioned on a first side of said interior space, said second portion being positioned on a second side of said interior space, said first and second portions being positioned such that a center column through said interior space does not have either said first or second portions of said heating assembly positioned therein; and
- a battery assembly operationally coupled to said heating assembly, said battery assembly providing electrical current to said heating assembly;
- wherein a pocket assembly coupled to said cover member, said pocket assembly dividing said cover assembly into a first and second portions, said pocket assembly being positioned in said center column, said pocket assembly having an opening adjacent to a top edge of said cover member, said pocket assembly being adapted for abutting a spine of the user; and
- a gel package positionable within said pocket assembly, said gel, said gel package providing support for the spine of the user when the user is in a reclined position abutting said assembly;
- wherein said gel package being removable from said pocket assembly, said gel package being adapted for being refrigerated such that said gel package providing a cooling surface area when positioned in said pocket assembly;
- wherein a first insulator member positioned between a first edge of said pocket assembly an a first portion of said cover member, said first insulator member providing a thermal barrier between said heating assembly and said gel package such that heat generated by said heating assembly is not conducted to the spine of the user when said gel package abuts the spine; and
- a second insulator member positioned between a second edge of said pocket assembly an a second portion of said cover member, said second insulator member providing a thermal barrier between said heating assembly and said gel package such that heat generated by said heating assembly is not conducted to the spine of the user when said gel package abuts the spine; and
- wherein a rheostat assembly operationally coupled to said heating assembly, said rheostat portion being for adjusting a quantity of heat generated by said heating assembly such that a temperature is adjustable by the user.

* * * * *